United States Patent [19]

Yamada et al.

[11] Patent Number: 5,759,528
[45] Date of Patent: Jun. 2, 1998

[54] TOPICAL COMPOSITION FOR PROMOTING TRANSDERMAL ABSORPTION OF THERAPEUTIC AGENTS

[75] Inventors: Eiichi Yamada; Shinji Hayashi, both of Tsukuba; Masao Takahashi; Shoji Fukushima, both of Machida, all of Japan

[73] Assignee: Institute for Advanced Skin Research, Inc., Kanagawa, Japan

[21] Appl. No.: 693,301

[22] PCT Filed: Feb. 17, 1995

[86] PCT No.: PCT/JP95/00233

§ 371 Date: Feb. 11, 1997

§ 102(e) Date: Feb. 11, 1997

[87] PCT Pub. No.: WO95/22351

PCT Pub. Date: Aug. 24, 1995

[30] Foreign Application Priority Data

Feb. 18, 1994 [JP] Japan ............... 6-021216
May 20, 1994 [JP] Japan ............... 6-106797

[51] Int. Cl.$^6$ ...................................... A61K 7/035
[52] U.S. Cl. ............. 424/69; 424/78.02; 424/78.03
[58] Field of Search .................. 424/69, 78.02, 424/78.03

[56] References Cited

U.S. PATENT DOCUMENTS

| | | | |
|---|---|---|---|
| 3,933,422 | 1/1976 | Saad | 8/10.1 |
| 3,961,044 | 6/1976 | Kelly et al. | 424/78 |
| 4,213,912 | 7/1980 | Varma | 552/514 |
| 4,866,201 | 9/1989 | Motojima et al. | 560/126 |

*Primary Examiner*—Terressa Mosley
*Attorney, Agent, or Firm*—Burns, Doane, Swecker & Mathis, L.L.P.

[57] ABSTRACT

A composition for topical application comprising at least one surfactant having a nitrogen atom in the moiety thereof and at least one compound selected from the group consisting of cyclohexane and the derivatives thereof, cyclohexene and the derivatives thereof, and cyclohexanone and the derivatives thereof.

8 Claims, No Drawings

TOPICAL COMPOSITION FOR PROMOTING TRANSDERMAL ABSORPTION OF THERAPEUTIC AGENTS

TECHNICAL FIELD

The present invention relates to a composition for topical application. More particularly, the present invention relates to a composition for topical application capable of dissolving the corneal layer of the skin at the surface of the skin acting as a barrier to prevent the invasion of foreign matter from outside the body and capable of preventing the leakage of humor etc. from inside the body and which promotes the absorption of a medicine from the skin. The present invention relates to a composition for topical application suitable for releasing a bioactive agent through the protective outer layer of the skin where it is applied and to the underlying tissue or the systemic circulation. Here, the term bioactive agent means a "skin agent effective for the skin" or a "treatment agent effective for the organs where cure is needed". The term "skin agent effective for the skin" means a chemical substance which has a beneficial topical effect when applied to the skin and has beautifying properties (for example, through protection of the skin against external factors or through improvement of the external appearance) or therapeutic properties (for example, through alleviation of the severity of a skin disease).

The term "treatment agent effective for the organs where cure is needed" means an agent which enters the systemic circulation and has a therapeutic effect when administered through intravenous injection, intramuscular injection, oral administration, rectal or buccal routes, and other various routes.

BACKGROUND ART

As the methods of administration of a medicinal ingredient, oral administration, administration by injection subcutaneously, intramuscularly, and intravenously, administration to the mucous membrane in the rectum or mouth, etc. are used in the past. Among these, oral administration is most general. However, in the case of oral administration, the medicinal ingredient is absorbed in large quantities in a short time frame, and therefore, it is difficult to control the concentration in the blood. Further, the absorbed medicinal ingredient sometimes loses its efficacy due to metabolis in the liver at the time of its first circulation. Further, in the case of an irritative medicinal ingredient, its administration easily causes side effects such as damage to the stomach or intestines and has numerous other problems. In recent years, to alleviate these side effects and problems, external preparations designed for transdermal administration have been developed. However, even with these external preparations, sufficient transdermal absorption of the medicinal ingredient is often not obtained and it is difficult to say that the objective has been sufficiently achieved. That is, the surface of the skin is called stratum corneum epidermidis skin and has the biological functions of preventing the intrusion of foreign matter from outside the body and preventing the leakage of humor from inside the body, and therefore, there was the problem that a sufficient transdermal absorption could not be obtained simply by mixing a medicinal ingredient into a substrate used in the past for external preparations.

To improve these problems, in recent years various keratolytic agents for promotion of transdermal absorption comprising keratolytic agents have been proposed and have been mixed in substrates of external preparations as a matter of routine. As such agents for promotion of transdermal absorption, there are known for example, dimethyl sulfoxide, dimethylformamide, dimethylacetamide, methyldecyl sulfoxide, etc. These cannot be said to be sufficient in terms of the effect of promoting transdermal absorption, safety, or feeling of use. Contrary to this, Japanese Unexamined Patent Publication (Kokai) No. 58-15910 describes the combination of cineole and a medicine, while Japanese Unexamined Patent Publication (Kokai) No. 63-77825 describes the combination of cineole, a nonionic surfactant, water, and a medicine so as to improve the safety and skin permeation of the medicine. Hifuka Kiyo (Dermatology Abstracts), Vol. 89, no. 2, pp. 267 to 271 (1994) reported on the use of limonene in a mixed solvent of water and ethanol as an absorption enhancing agent for lidocaine, while Japanese Unexamined Patent Publication (Kokai) No. 63-208536 disclosed a technique of using as effective ingredients one or more types of anionic surfactants and one or more types of a surfactant other than an anionic surfactant having a nitrogen atom in its moiety. U.S. Pat. No. 4,411,843 proposed the enhancer of transdermal absorption by an amine oxide and hydrophobic to hydrophilic medicines, while Japanese Unexamined Patent Publication (Kokai) No. 5-148158 deemed that the barrier to transdermal absorption was a two-stage barrier mechanism of not only the stratum corneum, but also the layer of living epidermal cells, discovered that N-lauroyl sarcosine was effective for the corneal layer and $\beta$-carotene and/or allantolactone for the layer of living epidermal cells and proposed to solve the above problems using the same. However, even with this, a sufficient transdermal absorption cannot be obtained.

Japanese Unexamined Patent Publication (Kokai) No. 61-85496 discloses the use of cineole and lauryl diethanolamide as a washing agent for textiles, plastics, metals, etc.; Japanese Unexamined Patent Publication (Kokai) No. 1-144495 discloses a detergent comprising a surfactant and terpene improved in rinsability for apparel, eating utensils, housing, hair, the body, etc.; and Japanese Unexamined Patent Publication (Kokai) No. 2-182793 discloses a washing agent comprising an alkylglycoside, an anionic surfactant, terpene, and a 3-isothiazolone derivative and with a high safety for apparel, the kitchen, housing, hair, and body, but these do not have any descriptions of the transdermal absorption of the compounds.

DISCLOSURE OF THE INVENTION

Accordingly, the object of the present invention is to solve the above problems and provide a composition for topical application which is superior in the effect of promotion of transdermal absorption of a medicinal ingredient, which is satisfactory in terms of safety and feeling of use, and does not require consideration of a two-stage barrier mechanism.

In accordance with the present invention, there is provided a composition for topical application comprising at least one surfactant having a nitrogen atom in its moiety and at least one compound selected from the group consisting of cyclohexane and the derivatives thereof, cyclohexene and the derivatives thereof, and cyclohexanone and the derivatives thereof.

In accordance with the present invention, there is also provided a composition for topical application further including at least one alkyl sulfate.

BEST MODE FOR CARRYING OUT THE INVENTION

The constitution of the present invention will now be explained.

The surfactant having a nitrogen atom in its moiety, may include a bipolar surfactant, a semipolar surfactant, a nonionic surfactant, and a cationic surfactant.

The semipolar surfactant compound among surfactants having a nitrogen atom in their moieties usable in the present invention may include those having the following formula (I):

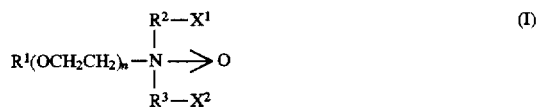

wherein, $R^1$ represents a $C_1$ to $C_{24}$ alkyl group or $C_2$ to $C_{24}$ alkenyl group, $R^2$ and $R^3$ independently represent a $C_1$ to $C_{10}$ alkylene group or $C_2$ to $C_{10}$ alkenylene group, $X^1$ and $X^2$ independently represent hydrogen or a hydroxyl group, and n is an integer of 0 to 3.

Examples of the semipolar surfactant are dimethylisopropylamine oxide, dimethyl-hexylamine oxide, dimethyloctylamine oxide, dimethyl-decylamine oxide, dimethylundecylamine oxide, dimethyl-laurylamine oxide, dimethylmyristylamine oxide, dimethyl-cetylamine oxide, dimethyloleylamine oxide, dimethyl-stearylamine oxide, dimethylbehenylamine oxide, dihydroxylethyllaurylamine oxide, dihydroxylethyl hydrogenated tallow alkylamine oxide, dimethyllaurylpolyoxyethyleneamine oxide, dimethyl coconut oil alkylamine oxide, didecylmethylamine oxide, etc. These may be used alone or in any combinations of two or more types.

Further, examples of the bipolar surfactant among surfactants having a nitrogen atom in their molecules usable in the present invention, are betaine lauryldimethylaminoacetate, betaine stearyldimethylamino-acetate, betaine stearyldihydroxylethylaminoacetate, betaine coconut oil alkyldimethylaminoacetate, lauryldiaminoethylglycine, betaine coconut oil alkylamide propyldimethylaminoacetate, betaine N-carboxymethyl-N-hydroxyethyl-2-alkylimidazolinium, betaine lauryldimethylaminopropylsulfonate, etc. These may be used alone or in any combinations of two or more types.

Further, examples of the anionic surfactant among surfactants having a nitrogen atom in their moieties usable in the present invention are lauryldiethanolamide, lauryldipolyoxyethylenamide, myristyldiethanolamide, myristyldipolyoxyethylenamide, oleyldiethanolamide, oleyldipolyoxyethyleneamide, stearyldiethanolamide, stearyldipolyoxyethylenamide, isostearyldiethanolamide, isostearyldipolyoxyethylen-amide, ricinoleyldiethanolamide, ricinoleyldipolyoxyethylenamide, coconut oil alkyldiethanolamide, coconut oil alkyldipolyoxyethylenamide, tallow alkyldiethanolamide, tallow alkyldipolyoxyethylenamide, hydrogenated tallow alkyldiethanolamide, hydrogenated tallow alkyldipolyoxyethylenamide, laurylmonoethanolamide, laurylmonopolyoxyethylenamide, palmitylmonoethanolamide, palmitylmonopolyoxyethylenamide, stearylmonoethanolamide, stearylmonopolyoxyethylenamide, coconut oil alkylmonoethanolamide, coconut oil alkylmonopolyoxyethylenamide, tallow alkylmonoethanolamide, tallow alkylmonopolyoxyethylenamide, hydrogenated tallow alkylmonoethanolamide, hydrogenated tallow alkylmonopolyoxyethylenamide, etc. These may be used alone or in any combinations of two or more types.

Further, examples of the cationic surfactant among surfactants having a nitrogen atom in their moieties usable in the present invention are octadecylamine acetate, tetradecylamine acetate, tallow alkyl propylenediamine acetate, octadecyltrimethylammonium chloride, tallow alkyl trimethylammonium chloride, dodecyltrimethylammonium chloride, coconut oil trimethylammonium chloride, hexadecyltrimethylammonium chloride, behenyltrimethylammonium chloride, N-hydroxyethyl-N-methyl-2-tallow alkylimidazolium chloride, coconut oil alkyldimethylbenzylammonium chloride, myristyldimethylbenzylammonium chloride, stearyldimethylbenzylaminonium chloride, dioleyldimethylammonium chloride, tripolyoxyethylene(3) dodecylmonomethylammonium chloride, coconut oil alkylisoquinolinium bromide, etc. These may be used alone or in any combinations of two or more types.

The cyclohexane derivatives usable in the present invention are represented by the formula (II):

wherein, $R^4$ independently represents a hydroxyl group, halogen atom, a $C_1$ to $C_{16}$ straight or branched alkyl group which may be substituted with a hydroxyl group or hydrogen atom, a benzyl group, a phenyl group, and —O— group wherein one single bond connects to a carbon constituting part of a cyclohexane ring and the other single bond connects to a carbon constituting part of a cyclohexane ring or another group $R^4$, and m is an integer of 0 to 4. More specifically, the examples are cyclohexane, methylcyclohexane, 1,1-dimethylcyclohexane, 1,2-dimethylcyclohexane, 1,3-dimethylcyclohexane, 1,4-dimethylcyclohexane, ethylcyclohexane, 1,2,3-trimethylcyclohexane, 1,1,3-trimethylcyclohexane, 1,2,4-trimethylcyclohexane, 1,3,5-trimethylcyclohexane, 1-ethyl-3-methylcyclohexane, 1-ethyl-1-methylcyclohexane, 1-ethyl-1,3-dimethylcyclohexane, 1-ethyl-3,5-dimethylcyclohexane, vinylcyclohexane, n-propylcyclohexane, isopropylcyclohexane, 1,1,3,5-tetramethylcyclohexane, 1,2,3,4-tetramethylcyclohexane, 1,2,4,5-tetramethylcyclohexane, 1,3,4,5-tetramethylcyclohexane, 1-methyl-3-n-propylcyclohexane, 1-isopropyl1-methylcyclohexane, 1-methyl-1-n-propylcyclohexane, 1-isopropyl-2-methylcyclohexane, 1-isopropyl-3-methylcyclohexane, 1-isopropyl-4-methylcyclohexane, 1-isopropyl-4,5-dimethylcyclohexane, 1,3-dimethyl-1-n-propylcyclohexane, n-butylcyclohexane, isobutylcyclohexane, sec-butylcyclohexane, tert-butylcyclohexane, 1,3-diethylcyclohexane, 1-butyl-2-ethylcyclohexane, n-amylcyclohexane, tert-amylcyclohexane, 1-amyl-2-methylcyclohexane, 1,4-diisopropylcyclohexane, n-hexylcyclohexane, n-heptylcyclohexane, n-octylcyclohexane, 1,4-di-sec-butylcyclohexane, n-dodecylcyclohexane, 1-dodecyl-2-methylcyclohexane, 1-dodecyl-3-methylcyclohexane, 1,4-pentylcyclohexane, n-tetradecylcyclohexane, n-hexadecylcyclohexane, phenylcyclohexane, 1-naphthylcyclohexane, 1,4-dibenzhydrylcyclohexane, chlorocyclohexane, 1,2-dibromocyclohexane, 2-chlor-1-methylcyclohexane, 1-tert-butyl-1-chlorcyclohexane, 1-hydroxymethyl-4-isopropenylcyclohexane, 1-methyl-3-hydroxy-4-isopropylcyclohexane (generic name: menthol), 1,4-oxide-p-menthane (generic name: 1,4-cineole), 1,8-oxide-p-menthane (generic name: 1,8-cineole), 1-methyl-4-isopropyl-cyclohexane (generic name: menthane), etc.

The cyclohexene derivatives usable in the present invention are represented by the general formula (III):

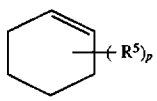

wherein, $R^5$ independently represents, a hydroxyl group, halogen atom, a $C_1$ to $C_{16}$ straight or branched alkyl group which may be substituted with a hydroxyl group or a halogen atom, a benzyl group or a phenyl group, and p is an integer of 0 to 4. More specifically, examples are the following compounds: cyclohexene, 1-methyl1-cyclohexene, 3-methyl-1-cyclohexene, 4-methyl-1-cyclohexene, 1,1-dimethyl-1-cyclohexene, 1,2-dimethyl-1-cyclohexene, 1,4-dimethyl-1-cyclohexene, 1,5-dimethyl-1-cyclohexene, 3,5-dimethyl-1-cyclohexene, 4,4-dimethyl-1-cyclohexene, 1-methyl-4-isopropenyl-1-cyclohexene (generic name: limonene), ethylidenecyclohexane, 1-ethyl-1-cyclohexene, 3-ethyl-1-cyclohexene, 4-ethyl-4-methyl-1-cyclohexene, 1-vinyl-1-cyclohexene, 4-vinyl-1-cyclohexene, 1,3,5-trimethyl-1-cyclohexene, 1-ethyl-3-methyl-1-cyclohexene, 2-ethyl-4-methyl-1-cyclohexene, 3-methyl-2-vinyl-1-cyclohexene, 1-methyl-3-vinyl-1-cyclohexene, 1-n-propyl-1-cyclohexene, 3-n-propyl-1-cyclohexene, 1-isopropyl-1-cyclohexene, 3-isopropyl-1-cyclohexene, 4-isopropyl-1-cyclohexene, 1-ethylidene-3-methyl-cyclohexane, allylcyclohexane, n-propylidene-cyclohexane, isopropylidenecyclohexane, 1-n-butyl-1-cyclohexene, 3-n-butyl-1-cyclohexene, 3-isobutyl-1-cyclohexene, 1-tert-butyl-1-cyclohexene, 4-tert-butyl-1-cyclohexene, 1,2,4,5-tetramethyl-1-cyclohexene, 1,1,3,5-tetramethyl-1-cyclohexene, 1-phenyl-1-cyclohexene, 3-phenyl-1-cyclohexene, 1-benzyl-1-cyclohexene, 3-benzyl-1-cyclohexene, 3-allyl-4-butadienyl-1-cyclohexene, 2-allylidene-1-methylenecyclohexane, 3-cyclohexylidene-2-methyl-1-propene, 1-methyl-4-hydroxypropyl-1-cyclohexene (generic name: α-terpineol), 1-chlor-1-cyclohexene, 3-chloro-1,4-dimethyl-1-cyclohexene, 3-chlor-1-isopropyl-1-cyclohexene, and 1-hydroxymethyl-4-isopropenyl-1-cyclohexene (generic name: perillyl alcohol).

The cyclohexanone derivatives usable in the present invention are represented by the formula (IV):

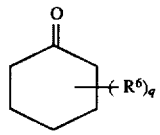

wherein, $R^6$ independently represents a hydroxyl group, halogen atom, a $C_1$ to $C_{16}$ straight or branched alkyl group which may be substituted with a hydroxyl group or halogen atom, benzyl group or phenyl group, and q is an integer of 0 to 4. More specifically, examples are: cyclohexanone, 2-methylcyclohexanone, 3-methylcyclohexanone, 4-methylcyclohexanone, 2,2-dimethylcyclohexanone, 2,6-dimethylcyclohexanone, 3,3-dimethylcyclohexanone, 3,4-dimethylcyclohexanone, 4,4-dimethylcyclohexanone, 2,4-dimethylcyclohexanone, 2,5-dimethylcyclohexanone, 3,5-dimethylcyclohexanone, 2-ethylcyclohexanone, 3-ethylcyclohexanone, 4-ethylcyclohexanone, 2,4,4-trimethylcyclohexanone, 2,4,6-trimethylcyclohexanone, 2,2,5-trimethylcyclohexanone, 2,2,6-trimethylcyclohexanone, 2,3,5-trimethylcyclohexanone, 3,3,4-trimethylcyclohexanone, 3,3,5-trimethylcyclohexanone, 3-ethyl-3-methylcyclohexanone, 2-propylcyclohexanone, 4-propylcyclohexanone, 2-isopropylcyclohexanone, 3-isopropylcyclohexanone, 4-isopropylcyclohexanone, 2,2,6,6-tetramethylcyclohexanone, 3,3,5,6-tetramethylcyclohexanone, 3,3,5,5-tetramethylcyclohexanone, 2,2-diethylcyclohexanone, 2-tert-butylcyclohexanone, 3-tert-butylcyclohexanone, 4-tert-butylcyclohexanone, 2-tert-butyl-6-methylcyclohexanone, 2-tert-butyl-5-methylcyclohexanone, 2-tert-butyl-4-methylcyclohexanone, 2-phenylcyclohexanone, 3-phenylcyclohexanone, 4-phenylcyclohexanone, 2-benzyl-4-methylcyclohexanone, 5,5-dimethyl-3-phenylcyclohexanone, cis-2,6-dibenzylcyclohexanone, 2,6-dibenzylcyclohexanone, 2-chlorcyclohexanone, 2-chlor-6,6-dimethyl-cyclohexanone, and 1-methyl-4-isopropyl-3-cyclohexanone (generic name: menthone).

The cyclohexanone derivatives usable in the present invention are, for example: oxycyclohexanone, 2-oxycyclohexanone (generic name: adipoin), 3-oxycyclohexanone, 4-oxycyclohexanone, 2-oxy-2-methylcyclohexanone, 2-oxy-5,5-dimethyl-cyclohexanone, 4-oxy-2,4,6-trimethylcyclohexanone, 2-oxy-3,3,6,6-tetramethylcyclohexanone, 4-oxy-4-methyl-3-phenylcyclohexanone, and 3,4,5-trioxycyclohexanone.

The alkyl sulfate freely usable in the present invention are, for example, compounds represented by the formula (V):

$$R^7OSO_3M \qquad (V)$$

wherein, $R^7$ is a $C_6$ to $C_{18}$ straight or branched alkyl group or $C_7$ to $C_{22}$ alkyl ether group and M represents Na, K, or an amine (for example, triethanolamine).

Examples of such alkyl sulfates are sodium decylsulfate, sodium lauryl sulfate, sodium myristyl sulfate, potassium decyl sulfate, potassium lauryl sulfate, triethanolamine lauryl sulfate, sodium lauryltriethoxy sulfate, etc.

The ratio by weight of the at least one surfactant having a nitrogen atom in the moiety thereof and the at least one compound selected from cyclohexane, cyclohexene, and cyclohexanone and their derivatives is preferably 100:0.5 to 2:100, more preferably from 100:5 to 20:100. The ratio by weight of the at least one surfactant having a nitrogen atom in the moiety thereof and the alkyl sulfate freely usable in the present invention is preferably 100:5 to 5:100, more preferably 100:10 to 50:100. Examples of the skin (that is, treatment or beautifying) agent usable in the composition for topical application according to the present invention are an antibacterial agent, antifungal agent, antiviral agent, nonsteroidal type antiinflammation agent, psoriasis treatment agent, antidermititus agent, antipruritic agent, antiwart agent, stratum corneum abration agent, local anesthetic agent, antierythema agent, antimetabolic agent, PMS agent, estrogenic agent, male hormone agent, skin softening agent, sun screen agent, emollient, antihistamine agent, antiacne agent, antiperspiration agent, or steroidal antiinflammation agent.

Examples of such a skin medicine, more specifically, are isoniazid, erythromycin, oxytetracyclin, clindamycin, chlorotetracyclin, cephalexin or cephalosporin antibiotic, 2-thiopyridine-N-oxide, tetracyclin, penicilling, penicillin V, iodine, iodine bactericide, lincomycin, chlorhexidine, chloramine antibacterial agent, sulfonamide antibacterial agent, hexachlorophene, benzoyl peroxide or aminoglucoside antibiotic; amphotericin B, gramicidin, griseofulvin, scopolamine, thiabendazole, nystatin, nitrofurantoin, 5-iodo-2-deoxyuridine; 5-fluorouracyl, propantheline bromide, mycophenolic acid, mesotrexylate, metatropin nitrate, metscopolamine bromide, 6-mercaptopurine; d,1-α- cyclopentylphenylacetoxymethyl-1-methylpyrrolidium chlorite, d,1-α-cyclopentylphenylacetoxymethyl-1-methylpyrrolidiniumdodecyl sulfate; antipyrine, diclofenac sodium, tranexamic acid, hydrocortisone, hydrocortisone-17-valerate, hydrocortisone-17-butylate, hydrocortisone-21-acetate, betamethasone valerate, triamcinoloneacetonide, fluocinonide, desonide, fluocinolone acetonide, dexamethasone, dexamethasone-21-phosphate, prednisolone, prednisolone-21-phosphate, haloprednone, indometacin, naproxen, phenoprofen, ibuprofen, alclofenac, phenylbutazone, sulindac, desoxysulindac, diflunisal, aspirin, mefenamic acid, benzocaine, procaine, propoxycaine, dibucaine, lidocaine, p-aminobenzoic acid, p-dimethylaminobenzoic acid, p-dimethylaminobenzoic acid alkyl esters; estradiol, testosterone, promogesterone; cyproheptadine hydrochloride; arbutin, kojic acid, diphenhydramine, hydroquinone, etc.

Further, the treatment agents which can be used mixed in the composition for topical application according to the present invention and can improve the skin absorption and pass through the skin to act in the systemic circulation, are, for example, an antibacterial agent, antifungal agent, antiviral agent, steroidal antiinflammation agent, nonsteroidal antiinflammation agent, β-blocker, antihypertension agent, antiangina agent, antiarrhythmic agent, vasodilator, antitussive, PMS agent, estrogenic agent, male hormone agent, muscular relaxant, or antiasthmatic agent, more specifically, isoniazid, lincomycin, chlorotetracyclin, erythromycin, tetracyclin, oxytetracyclin, chlorotetracyclin, 2-thiopyridine-N-oxide, iodine, iodine bactericide, penicillin antibiotic, cephalosporin antibiotic, penicillin G, penicillin V, cephalexin, cefoxitin, sulfonamide antibacterial agent, aminoglucoside antibiotic, nitrofurantoin, nystatin, amphotericin B, 5-iodo-2-deoxyuridine, N-formimidoylthienamycin-1-hydrate, 1-ethyl-6-fluoro-1,4-dihydro-4-oxo-7-(1-piperadinyl)-3-quinolinecarboxylic acid, phosphomycin, novabiocin, cycloserine, cephamycin C, griseofulvin; hydrocortisone, hydrocortisone-17-valerate, hydrocortisone-17-butyrate, hydrocortisone-21-acetate, betamethasone valerate, triamcinoloneacetonide, fluocinonide, desonide, fluocinolone acetonide, dexamethasone, dexamethasone-21-phosphate, prednisolone, prednisolone-21-phosphate, haloprednone; antipyrine, indometacin, diclofenac sodium, tranexemic acid, naproxen, phenoprofen, ibuprofen, alclofenac, phenylbutazone, sulindac, desoxysulindac, diflunisal, aspirin, mefenamic acid, clonidine, α-methyldopa, estradiol, progesterone, testosterone, propranolol, bufetolol, metoprolol, nadolol, sotalol, alprenolol, oxprenolol carteolol, lavetalol, atenolol, pindolol, timolol, timololmaleate, nitroglycerine, erythritoltetranitrate, isosorbitodinitrate, mannitolhexanitrate, pentaerythritoltetranitrate, papaverine, dipyridamole, betahistine, cyclobenzapurine hydrochloride, diazepam, chromoglycerine acid, etc. These medicinal ingredients are quickly absorbed by the skin when formulated into the composition for topical application of the present invention and being coated on the skin. If the medicinal ingredient is aimed at a local action, it permeates deep into the skin and exhibits a superior effect, while if the medicinal ingredient is aimed at a systemic action, the medicinal ingredient to the blood, and therefore, similarly exhibits a superior effect. The subjects on which it is used are not limited to human beings and may include domestic animals, dogs, cats, and other warm blooded animals etc. The amount of the medicinal ingredient mixed in should be one sufficient for exhibiting the medicinal effect and differs depending on the type of the medicinal ingredient, body weight of the patient, symptoms, etc., but in general is $1.25\times10^{-5}$ to $10^4$ parts by weight of the composition for local application per part by weight of the medicinal ingredient, more preferably $2\times10^{-4}$ to $5\times10^2$ parts by weight.

The composition for topical application according to the present invention may be suitably mixed with a medicinal ingredient and may be used as it is. Considering the feeling in use, the ease of application, etc. generally it is preferable to use the ingredient formulated into a suitable skin application, for example, a cream preparation, ointment preparation, gel preparation, lotion preparation, emulsion, adhesive tape agent, or other substrate. The amount of the ingredient in the skin application differs depending on the type of the medicinal ingredient, but is preferably generally as follows: that is, the composition for topical application is included in the skin external application in an amount of 0.001 to 10% by weight, more preferably 0.01 to 5% by weight, while the medicinal ingredient is included in an amount of 0.001 to 80% by weight, more preferably 0.01 to 50% by weight.

The composition for topical application including a medicinal ingredient according to the present invention may include, in addition to the above-mentioned essential ingredients, any other ingredients generally formulated into drugs, quasi-drugs, cosmetics, etc.

Examples of these ingredients are polyhydric alcohols, oils, waxes, acids, alkalis, cationic, noionic, anionic, and bipolar surfactants including a nitrogen atom in their moieties, powders, pigments, dyes, preservative and antibacterial agents, antioxidants, UV absorbants, chelating agents, water-soluble polymers, montmorillonite, alcohols, solvents, perfumes, etc.

EXAMPLES

The present invention will now be further illustrated in detail by, but is by no means limited to, the following Examples, wherein "parts" are all by weight unless otherwise noted.

Example 1-1

Aqueous solutions or aqueous suspensions of combinations of surfactants and cyclohexane and/or cyclohexene and/or cyclohexanone derivatives were tested for stratum corneum decomposition. The results are shown in Table 1-1. In all combinations, there was noticeable stratum corneum decomposition. Further, effective stratum corneum decomposition was exhibited even when the concentration of the aqueous solution was a low concentration of 0.01 mM.

Comparative Example 1-1

Aqueous solutions or aqueous suspensions of combinations of betaine and sulfate salts were tested for stratum corneum decomposition. The results are shown in Table 1-2. In all combinations, there was stratum corneum decomposition, but not to the extent of Example 1-1.

Comparative Example 1-2

Aqueous solutions or aqueous suspensions of combinations of amine oxides and various sulfate salts were tested for their stratum corneum decomposition. The results are shown in Table 1-3. In all combinations, there was stratum corneum decomposition, but not to the extent of Example 1-1.

Performance Evaluation Test 1

Stratum corneum decomposition was evaluated using the stratum corneum taken from guinea pigs. The stratum corneum was sampled in the following manner. The back of a guinea pig was depilated by shears and a depilatory, the guinea pig was sacrificed when the erythema subsided, then the entire skin was removed by scissors. The subcutaneous fat of the reverse side of the skin was removed by scissors, then the skin was immersed in 60° C. warm water for one minute and then cooled by ice. The epidermis was then cleanly removed by tweezers and a spatula. The epidermis was then treated by 0.1% trypsin in a phosphate buffer (pH 7.6) at 37° C. for one hour to digest the living cells, then was rinsed and dried to obtain the stratum corneum. The stratum corneum decomposition test was performed by the following method. The stratum corneum was cut into a 1×1 cm square, then immersed in 10 ml of the test solution and observed as to its state in a 32° C. constant temperature tank over the following days. The results of the evaluation are shown by the following symbols:

No change in shape of stratum corneum

+1: Stratum corneum somewhat decomposed

+2: Stratum corneum considerably decomposed

+3: Stratum corneum almost completely decomposed c: Existence of stratum corneum no longer observed

TABLE 1-1

(Example 1-1)

| Surfactant having nitrogen atom in moiety | Cyclohexane, cyclohexene and cyclohexanone derivative | Concentration (mM/l) | Days elapsed | | | |
|---|---|---|---|---|---|---|
| | | | 1 | 3 | 8 | 15 |
| Dimethyl laurylpoly oxyethylene amine oxide | 1-methyl-3-hydroxy-4-isopropyl cyclohexane | 5/5 | +2 | +3 | +3 | +3 |
| Dimethyl lauryl amine oxide | 1-methyl-4-isopropenyl-1-cyclohexene | 5/5 | c | c | c | c |
| Dimethyl lauryl amine oxide | 2,6-dimethyl cyclohexanone | 5/5 | +3 | c | c | c |
| Betaine lauryl dimethylamino acetate | 1-methyl-4-hydroxypropyl 1-cyclohexene | 5/5 | +2 | +2 | +3 | +3 |
| Lauryl diethanol amide | 1,4-oxide 1-methyl-4-propyl-cyclohexene | 5/5 | +2 | +3 | +3 | +3 |
| Tetradecyl amineacetate | 1-methyl-3-hydroxy-3-isopropyl cyclohexane | 5/5 | +2 | +2 | +3 | c |

TABLE 1-2

(Comparative Example 1-1)

| Betaine | Sulfate | Concentration (mM/l) | Days elapsed | | | |
|---|---|---|---|---|---|---|
| | | | 1 | 3 | 8 | 15 |
| Betaine lauryl dimethylamino acetate | Sodium lauryl sulfate | 5/5 | — | +2 | +3 | +3 |
| Betaine N-carboxymethyl-N-hydroxyethyl-2-alkylimid-azolinium | Sodium lauryl sulfate | 5/5 | — | +1 | +2 | +3 |

TABLE 1-3

(Comparative Example 1-2)

| Amino oxide | Sulfate | Concentration (mM/l) | Days elapsed | | | |
|---|---|---|---|---|---|---|
| | | | 1 | 3 | 8 | 15 |
| Dimethyl laurylamine oxide | Sodium lauryl sulfate | 5/5 | +1 | +2 | +3 | c |
| Dimethyl laurylamine oxide | Sodium lauryl polyoxy ethylene sulfate | 5/5 | +1 | +2 | +2 | +3 |

Reference Example 2-1

235 g of 2-ethylhexylmethacrylate, 25 g of N-vinylpyrrolidone, 38 mg of hexanedioldimethacrylate, and 260 g of ethyl acetate were added to a reaction vessel and warmed to 60° C. 1 g of octanoyl peroxide dissolved in 50 g of cyclohexane was placed into a dropping tank 1, 175 g of ethyl acetate was placed in a dropping tank 2, and these were added dropwise for 2 hours. The resulting solution was then held constant for 10 hours so as to polymerize to obtain a methacrylic adhesive substrate with a solid content of 35% by weight.

Example 2-1. Transdermal-Absorption Agent 0.3 g of a tetrahydrofuran solution containing 0.175 g of dimethyllaurylamine oxide and 0.175 g of 1-methyl-4-isopropenyl-1-cyclohexene and 24 g of ethyl acetate were added to 100 g of the adhesive substrate solution obtained in Reference Example 2-1. This was then homogeneously mixed to obtain a transdermal absorption agent solution.

Example 2-2. Tape Agent 0.7 g of a tetrahydrofuran solution containing 2.1 g of indometacin was added to the transdermal absorption agent solution obtained in Example 2-1. This was then homogeneously mixed to obtain a skin external application. The skin external application was coated on a release sheet comprised of 38 μm thick polyethyleneterephthalate film treated by silicone so as to obtain a thickness of the ointment layer after drying of 80 μm. The coated layer was dried at 60° C. for 30 minutes. Next, a 34 μm thick support comprised of a polyethyleneterephthalate-ethylene-vinyl acetate copolymer laminate film was placed over the top surface of the ointment layer to prepare a tape agent.

Comparative Example 2-1. Tape Agent

The same procedure was followed as in Reference Example 2-1 and Example 2-2 to prepare a tape agent except that the 100 g of the adhesive substrate solution in Example 2-1 was augmented by 0.3 g of a tetrahydrofuran solution containing 0.175 g of dimethyllaurylamine oxide and 24 g of ethyl acetate which were then homogeneously mixed to obtain the solution of the transdermal absorption agent.

Comparative Example 2-2. Tape Agent

The same procedure was followed as in Reference Example 2-1 and Example 2-2 to prepare a tape agent except that the 100 g of the adhesive substrate solution in Example 2-1 was augmented by 0.3 g of a tetrahydrofuran solution containing 0.175 g of 1-methyl-4-isopropenyl-1- cyclohexene and 24 g of ethyl acetate which were then homogeneously mixed to obtain the solution of the transdermal absorption agent.

Performance Evaluation Test (Tape Agent)

The back of an 8-week old male wistar rat was depilated. A circular (1 cm diameter) test piece of the tape agent was adhered to the depilated location. This was peeled off and recovered after 24 hours. The number of repetitions was made six times for each tape agent. The recovered test pieces were extracted by methanol. The amount of the medicine remaining in the tape agent was measured by the high pressure liquid chromatography method. The difference between the initial amount of the medicine in the tape agent and the amount remaining after the test was used as the amount of transfer of the medicine to the skin of the rat over 24 hours. The ratio of the amount of transfer with respect to the initial amount of the medicine was used as the transdermal absorption rate. Table 2-1 shows the results.

TABLE 2-1

Transdermal Absorption Rate of Medicine

| Tape agent | Transdermal absorption rate (wt %) |
| --- | --- |
| Example 2-2 | 50.0 |
| Comparative Example 2-1 | 5.2 |
| Comparative Example 2-2 | 6.8 |

In Table 2-1, it is seen that the tape agent of Example 2-2 including the composition for local application of the present invention exhibits an approximately 10-fold transdermal absorption rate compared with the tape agents of Comparative Examples 2-1 to 2-2 containing one of these.

Example 3-1. Cream

| (1) Dexamethasone | 0.025% |
| --- | --- |
| (2) Propyleneglycol | 8.0% |
| (3) Glycerol | 5.0% |
| (4) Liquid paraffin | 1.0% |
| (5) Diisopropyl adipate | 3.0% |
| (6) Dimethyllaurylamine oxide | 0.12% |
| (7) 1-methyl-4-isopropenyl-cyclohexene | 0.12% |
| (8) Glycerol monofatty acid ester | 1.5% |
| (9) Preservative | q.s. |
| (10) Clay mineral (bentonite) | 6.0% |
| (11) Purified water | Balance |

The above composition was prepared to prepare a cream. First, (1), (4), (8), and (9) were added to (5) and heated to 70° C. to melt and mix the same. The result was used as the Composition A. Next, (6) and (7) were added to part of (11) to dissolve them and then (2) and (3) were added and mixed. The result was used as the Composition B. While holding the temperature to 70° C. and stirring the Composition B, the Composition A was gradually added, preliminarily emulsified, then emulsified by a homomixer. The result was added with stirring to the remainder of (11) in which (10) was added and dispersed and cooled to obtain a cream.

Example 3-2. Cream

A similar cream as in Example 3-1 was prepared and tested except that the 1-methyl-4-isopropenyl-1-cyclohexene in Example 3-1 was replaced by 1-methyl-4-isopropyl-3-cyclohexanone.

Example 3-3. Cream

A similar cream as in Example 3-1 was prepared and tested except that the 1-methyl-4-isopropenyl-1-cyclohexene in Example 3-1 was replaced by 1-methyl-3-hydroxy-4-isopropyl-cyclohexane.

Example 3-4. Cream

A similar cream as in Example 3-1 was prepared and tested except that the 1-methyl-4-isopropenyl-1-cyclohexene in Example 3-1 was replaced by 1,8-oxide-p-menthane.

Comparative Example 3-1. Cream

| (1) Dexamethasone | 0.025% |
| --- | --- |
| (2) Propyleneglycol | 8.0% |
| (3) Glycerol | 5.0% |
| (4) Liquid paraffin | 1.0% |
| (5) Diisopropyl adipate | 3.0% |
| (6) Glycerol monofatty acid ester | 1.5% |
| (7) Preservative | q.s. |
| (8) Clay mineral (bentonite) | 6.0% |
| (9) Purified water | Balance |

The cream was prepared in accordance with Example 3-1.

Performance Evaluation Test (Cream)

The vasoconstrictive actions of the creams prepared in Examples 3-1 to 3-4 and Comparative Example 3-1 were compared.

The upper backs of 10 healthy male subjects were coated and adhered with randomly allocated creams prepared in Examples 3-1 to 3-4 and Comparative Example 3-1 and the above five types of creams not including dexamethasone using batch test use adhesive tape (made by Torii Yakuhin). After 4 hours, the adhesive tapes were peeled off and the test samples removed, then the areas were allowed to stand for another four hours before judgement was made.

The judgement criteria were based on the pallor accompanying the vasoconstrictive action of the steroid. The mean score was found for each substrate using "remarkable pallor" (score 2), "clear pallors" (score 1), "faint pallor" (score 0.5), and "no change" (score 0). The results are shown in Table 3-1.

TABLE 3-1

| Cream agent | Mean score after 4 hours |
| --- | --- |
| Example 3-1 | 1.9 |
| Example 3-2 | 1.85 |
| Example 3-3 | 1.8 |
| Example 3-4 | 1.75 |
| comparative Example 3-1 | 0.9 |
| System of Example 3-1 minus dexamethasone | 0 |
| System of Example 3-2 minus dexamethasone | 0 |
| System of Example 3-3 minus dexamethasone | 0 |
| System of Example 3-4 minus dexamethasone | 0 |
| System of Comparative Example 3-1 minus dexamethasone | 0 |

As clear from Table 3-1, the creams of Example 3-1 to 3-4 are superior in vasoconstrictive action.

Example 4-1. Gel

| (1) Indometacin | 1.0% |
| --- | --- |
| (2) Ethyl alcohol | 50.0% |
| (3) Carboxylvinyl polymer | 1.2% |

-continued

| | |
|---|---|
| (4) Polyoxyethylene hydrogenated castor oil | 1.5% |
| (5) Betaine lauryldimethylaminopropyl-sulfonate | 0.8% |
| (6) 1-methyl-4-isopropenyl-1-cyclohexene | 0.8% |
| (7) Diisopropanolamine | 0.35% |
| (8) Purified water | Balance |

The above composition was prepared to make a gel. First, (5) and (6) were dissolved in (8), then (3) was added and dispersed well. To this was added (1) and (4) added to and dissolved in (2) and the two mixed well. Further, (7) was added to the mixture which was then mixed and stirred well to obtain a gel.

Example 4-2. Gel

The same type of gel as in Example 4-1 was prepared and tested except that the 1-methyl-4-isopropenyl-1-cyclohexene of Example 4-1 was replaced with 2,6-dimethylcyclohexanone.

Example 4-3. Gel

The same type of gel as in Example 4-1 was prepared and tested except that the 1-methyl-4-isopropenyl-1-cyclohexene of Example 4-1 was replaced with 1-methyl-3-hydroxy-4-isopropyl-cyclohexane.

Comparative Example 4-1. Gel

| | |
|---|---|
| (1) Indometacin | 1.0% |
| (2) Ethyl alcohol | 50.0% |
| (3) Carboxylvinyl polymer | 1.2% |
| (4) Polyoxyethylene hydrogenated castor oil | 1.5% |
| (5) Diisopropanolamine | 0.35% |
| (6) Purified water | Balance |

The gel was prepared in accordance with Example 4-1.

Comparative Example 4-2. Ointment

Commercially available ointment containing 1% indometacin (gelatinous external preparation).

Performance Evaluation Test

The above-mentioned gel substrate was tested for the rate of suppression of carrageenin edema so as to investigate its medicinal effect. Specifically, using groups of five 8-week old Wister male rats, first the volumes of the right posterior legs of the rats of the groups were measured using a rat posterior leg podedema volume measurement device KM-357 (made by Natsume Seisakusho), next 0.2 g portions of the sample were coated on the right posterior legs of the rats. After 2 hours, 0.05 ml portions of 1% carrageenin sodium salt were injected subcutaneously at the same locations. Three hours after the injection of the carrageenin sodium salt, the volumes of the right posterior legs were measured. The difference with the volumes of the right posterior legs before the coating of the sample was used as the podedema volume, then the following formula was used to calculate the rate of suppression of podedema.

Rate of suppression of podedema (%)=(Vc−Vt)/Vc×100 where, Vc and Vt are the mean podedema volumes of the control group (no test sample coated) and the group on which the test sample was coated.

The above test results are shown in Table 4-1.

TABLE 4-1

| Rate of Suppression of Carrageenin Podedema (%) | |
|---|---|
| Example 4-1 | 62.0 |
| Example 4-2 | 61.6 |
| Example 4-3 | 60.0 |
| Comparative Example 4-1 | 10.8 |
| Comparative Example 4-2 | 8.3 |

As clear from Table 4-1, the gel substrates of Examples 4-1 to 4-3 containing the composition for local application of the present invention are superior in the action for suppressing carrageenin edema.

Example 5-1. Transdermal Absorption Agent

Mixed aqueous solutions of fixed concentrations of antipyrine and different concentrations of dimethyllaurylamine oxide and 1-methyl-4-isopropenyl-1-cyclohexene were prepared to test the transdermal absorption of antipyrine.

Example 5-2. Transdermal Absorption Agent

A similar test was performed as in Example 5-1 except that the concentration of dimethyllaurylamine oxide in Example 5-1 was made constant and the 1-methyl-4-isopropenyl-1-cyclohexene was replaced with 1-methyl-3-hydroxy-4-isopropyl-cyclohexane (concentration: 0.1% by weight).

Example 5-3. Transdermal Absorption Agent

A similar test was performed as in Example 5-1 except that the concentration of dimethyllaurylamine oxide in Example 5-1 was made constant and the 1-methyl-4-isopropenyl-1-cyclohexene was replaced with 1-methyl-4-isopropyl-cyclohexane (concentration: 0.1% by weight).

Example 5-4 Transdermal Absorption Agent

A similar test was performed as in Example 5-1 except that the concentration of dimethyllaurylamine oxide in Example 5-1 was made constant and the 1-methyl-4-isopropenyl-1-cyclohexene was replaced with 1,4-oxide-1-methyl-4-propyl-cyclohexane (concentration: 0.1% by weight).

Example 5-5. Transdermal Absorption Agent

A similar test was performed as in Example 5-1 except that the concentration of dimethyllaurylamine oxide in Example 5-1 was made constant and the 1-methyl-4-isopropenyl-1-cyclohexene was replaced with 2-tert-butylcyclohexanone (concentration: 0.1% by weight).

Example 5-6. Transdermal Absorption Agent

Mixed aqueous solutions of different concentrations of dimethyllaurylamine oxide and 1-methyl-4-isopropenyl-1-cyclohexene and sodium lauryl sulfate were prepared to test the transdermal absorption of seven types of medicines.

Comparative Example 5-1. Transdermal Absorption Agent

A similar test was performed as in Example 5-1 except that the concentration of dimethyllaurylamine oxide in Example 5-1 was made constant and the 1-methyl-4-isopropenyl-1-cyclohexene was replaced with 1-methyl-4-isopropyl-1,3-cyclohexadiene (generic name: α-terpinene) (concentration: 0.1% by weight).

Comparative Example 5-2. Transdermal Absorption Agent

The same procedure was followed as in Example 5-1 to prepare an antipyrine aqueous solution not containing either of dimethyllaurylamine oxide or 1-methyl-4-isopropenyl-1-cyclohexene and an antipyrine aqueous solution containing only one of dimethyllaurylamine oxide or 1-methyl-4-isopropenyl-1-cyclohexene and test the transdermal absorption of antipyrine.

Performance Evaluation Test (Transdermal Absorption Agent)

Pieces of skin of 7 to 14 week old hairless rats were attached to a Franz type diffusion cells containing 1 ml of donor side test solution and 5.2 ml of receiver side phosphate buffer and having a medicine contact area of 0.785 cm² (diameter of 1 cm). The diffusion cells were placed at a room temperature of 32° C. The test solution was drained off 2, 4, 8, and 24 hours after application to the skin and replaced by the same amount of a fresh phosphate buffer. A comparison was made by the percent permeation after 10 hours. The values are mean values of three tests of the skin of the same rat. Table 5-1, Table 5-2, Table 5-3, and Table 5-4 show the results.

TABLE 5-1

(Example 5-1. Transdermal Absorption Agent)
Percent Permeation of 2 wt % antipyrine at 10th Hour

| | | Dimethyllauryl amine oxide (wt %) | | | | | | | |
|---|---|---|---|---|---|---|---|---|---|
| | | 1.25 | 1.00 | 0.75 | 0.50 | 0.20 | 0.16 | 0.11 | 0.07 |
| 1-methyl-4-isopropenyl-1-cyclohexene (wt %) | 0.20 | — | 44.8 | — | — | — | — | — | — |
| | 0.16 | 48.9 | 43.4 | 40.7 | 37.7 | 33.9 | — | — | — |
| | 0.12 | — | — | — | — | 32.8 | — | — | — |
| | 0.10 | — | 39.4 | — | — | — | — | — | — |
| | 0.09 | — | — | — | — | — | 16.8 | — | — |
| | 0.07 | — | — | — | — | — | — | 12.9 | — |
| | 0.05 | — | 33.9 | — | — | — | — | — | — |
| | 0.04 | — | — | — | — | — | — | — | 8.9 |

TABLE 5-2

(Example 5-1 to 5-5, Comparative Example 5-1;
Transdermal Absorption Agents)
Percent Permeation of 2 wt % Antipyrine at 10th Hour

| | | Dimethyllauryl amineoxide (0.20 wt %) |
|---|---|---|
| Example 5-2: | 1-methyl-3-hydroxy-4-isopropyl-cyclohexene | 28.5 |
| Example 5-3: | 1-methyl-4-isopropyl-3-cyclohexanone | 14.9 |
| Example 5-4: | 1,8-oxide-1-methyl-4-propyl-cyclohexane | 12.2 |
| Example 5-5: | 2-tert-butylcyclohexanone | 9.5 |
| Comparative Example 5-1: | 1-methyl-4-isopropyl-1,3-cyclohexadiene (0.10 wt %) | 6.8 |

TABLE 5-3

(Example 5-6. Transdermal Absorption Agent)
Percent Permeation of 2 wt % Medicine at 10th Hour

| | (1.70 wt %) 1-methyl-4-isopropenyl-1-cyclohexene (0.34 wt %) | Dimethyllauryl amino oxide Sodium lauryl sulfate (0.72 pwt %) | (0.86 wt %) 1-methyl-4-isopropenyl 1-cyclohexene (0.68 wt %) + Sodium lauryl sulfate (0.36 wt %) |
|---|---|---|---|
| Isoniazid | 100 | 25 | — |
| Kojic acid | 100 | 7.5 | — |
| Albutin | 60 | 7.5 | — |
| Diphenhydramine | 40 | 5 | — |
| Betahistine | 75 | 6 | — |
| Methopulol | 85 | 10 | — |
| Antipyrine | 100 | 44 | 100 |

TABLE 5-4

(Comparative Example 5-2. Absorption Agent)
Percent Permeation of 2 wt % Antipyrine at 10th Hour

| | | |
|---|---|---|
| Deionized water | | 0.9 |
| Deionized water/ethanol = 1/2 | | 0.3 |
| 1-methyl-4-isopropenyl-1-cyclohexene (0.15 wt %, water/ethanol = 1/2) | | 1.0 |
| Dimethyllauryl amine oxide (wt %) | 1.80 | 7.7 |
| | 1.40 | 7.1 |
| | 1.00 | 6.5 |
| | 0.60 | 5.8 |
| | 0.20 | 4.0 |
| | 0.10 | 2.1 |

As clear from Tables 5-1 to 5-4, the transdermal absorption agents of Example 5-1 to 5-5 including the composition for local application of the present invention are superior to Comparative Examples 5-1 to 5-2 in the action of promoting the transdermal absorption of antipyrine. The presence of ethanol did not have any serious effect on the permeation of the medicine.

We claim:

1. An external skin treatment composition comprising a surfactant having a nitrogen atom in the moiety thereof and a compound selected from the group consisting of cylcohexane, derivatives of cyclohexane, cyclohexene, derivatives of cyclohexene, cyclohexanone and derivatives of cyclohexanone.

2. A composition as claimed in claim 1, further comprising an alkyl sulfate.

3. A composition as claimed in claim 1, wherein the surfactant having a nitrogen atom in the moiety is an amine oxide.

4. A composition as claimed in claim 1, wherein the surfactant having a nitrogen atom in the moiety thereof is represented by the formula (I):

wherein, $R^1$ represents an alkyl group having 1 to 24 carbon atoms or an alkenyl group having 2 to 24 carbon atoms, $R^2$ and $R^3$ represent independently an alkylene group having 1 to 10 carbon atoms or alkenylene group having 2 to 10 carbon atoms, $X^1$ and $X^2$ represent independently hydrogen or a hydroxyl group, and n is an integer of 0 to 3.

5. A composition as claimed in 1, wherein the cyclohexane derivative is represented by the formula II:

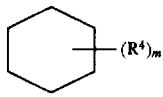 (II)

wherein, $R^4$ independently represents a hydroxyl group, a halogen atom, a straight or branched chain alkyl group having 1 to 16 carbon atoms or a straight or branched alkyl group having 1 to 16 carbon atoms which is substituted with a hydroxyl group or a halogen atom, a benzyl group, or a phenyl group, or an —O— group wherein one single bond connects to carbon constituting part of a cyclohexane ring and the other single bond connects to carbon constituting part of a cyclohexane ring or another group $R^4$, and m is an integer of 0 to 4.

6. A composition as claimed in claim 1, wherein the cyclohexene derivative is represented by the formula (III):

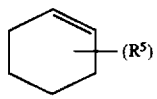 (III)

wherein, $R^5$ independently represents a hydroxyl group, a halogen atom, a straight or branched alkyl group having 1 to 16 carbon atoms or a straight or branched alkyl group having 1 to 16 carbon atoms which is substituted with a hydroxyl group or a halogen atom, a benzyl group, or a phenyl group, and p is an integer of 0 to 4.

7. A composition as claimed in claim 1, wherein the cyclohexanone derivative is represented by the formula (IV):

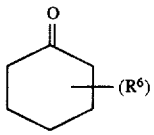 (IV)

wherein, $R^6$ independently represents a hydroxyl group, a halogen atom, a straight or branched alkyl group having 1 to 16 carbon atoms or a straight or branched alkyl group having 1 to 16 carbon atoms which is substituted with a hydroxyl group or halogen atom, a benzyl group, or a phenyl group, and q is an integer of 0 to 4.

8. A composition as claimed in claim 2, wherein the alkyl sulfate is represented by the formula (V):

$$R^7OSO_3M \qquad (V)$$

wherein, $R^7$ is a straight or branched alkyl group having 6 to 18 carbon atoms or an alkyl ether group having 7 to 22 carbon atoms and M represents Na, K, or an amine.

* * * * *